United States Patent [19]
Wolf et al.

[11] Patent Number: 5,810,863
[45] Date of Patent: Sep. 22, 1998

[54] TROCAR INCLUDING AN OBTURATOR WITH A REMOVABLE KNIFE

[75] Inventors: Philip L. Wolf, San Antonio; Mark S. Hickman, New Braunfels, both of Tex.

[73] Assignee: Moser Medical, Houston, Tex.

[21] Appl. No.: 659,421

[22] Filed: Jun. 6, 1996

(Under 37 CFR 1.47)

[51] Int. Cl.⁶ .................................................. A61B 71/34
[52] U.S. Cl. ........................................ 606/185; 606/167
[58] Field of Search ..................... 604/164, 264; 606/1, 108, 167, 184, 185, 213

[56] References Cited

U.S. PATENT DOCUMENTS

| | | |
|---|---|---|
| 3,097,646 | 7/1963 | Scislowicz . |
| 3,097,647 | 7/1963 | Roehr . |
| 3,313,299 | 4/1967 | Spademan . |
| 3,454,006 | 7/1969 | Langdon . |
| 3,613,684 | 10/1971 | Sheridan . |
| 3,989,049 | 11/1976 | Yoon . |
| 3,994,287 | 11/1976 | Turp et al. . |
| 4,177,814 | 12/1979 | Knepshield et al. . |
| 4,254,762 | 3/1981 | Yoon . |
| 4,535,773 | 8/1985 | Yoon . |
| 4,601,710 | 7/1986 | Moll . |
| 4,654,030 | 3/1987 | Moll et al. . |
| 4,788,976 | 12/1988 | Dee . |
| 4,931,042 | 6/1990 | Holmes et al. . |
| 5,030,206 | 7/1991 | Lander . |
| 5,055,106 | 10/1991 | Lungren . |
| 5,405,328 | 4/1995 | Vidal et al. .............................. 604/158 |
| 5,417,705 | 5/1995 | Maber et al. ........................... 606/185 |
| 5,522,833 | 6/1996 | Stephens et al. ....................... 606/185 |
| 5,534,009 | 7/1996 | Lander . |
| 5,620,456 | 4/1997 | Sauer et al. ............................ 606/185 |

OTHER PUBLICATIONS

"Product Directory", Surgeons' Reference™ For Minimally Invasive Surgery Products™, 2nd Edition, Sep. 1995, pp. II–202–II–223.

*Primary Examiner*—Glenn K. Dawson
*Attorney, Agent, or Firm*—Christopher Makay; Donald Comuzzi; James Ruland

[57] ABSTRACT

An obturator for a trocar having a shaft, pin, and removable knife. The pin mounts to the shaft and secures the knife thereto.

7 Claims, 10 Drawing Sheets

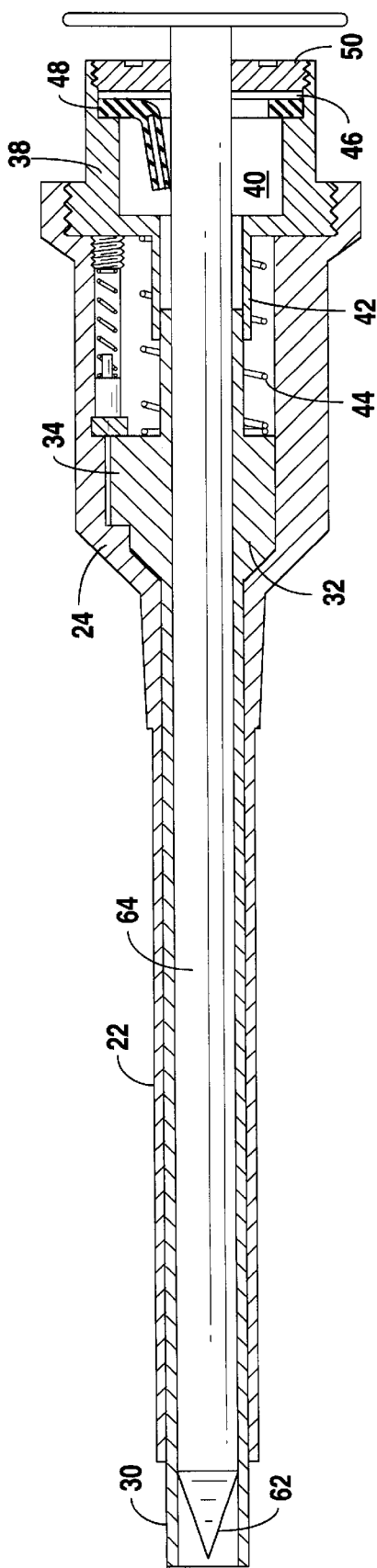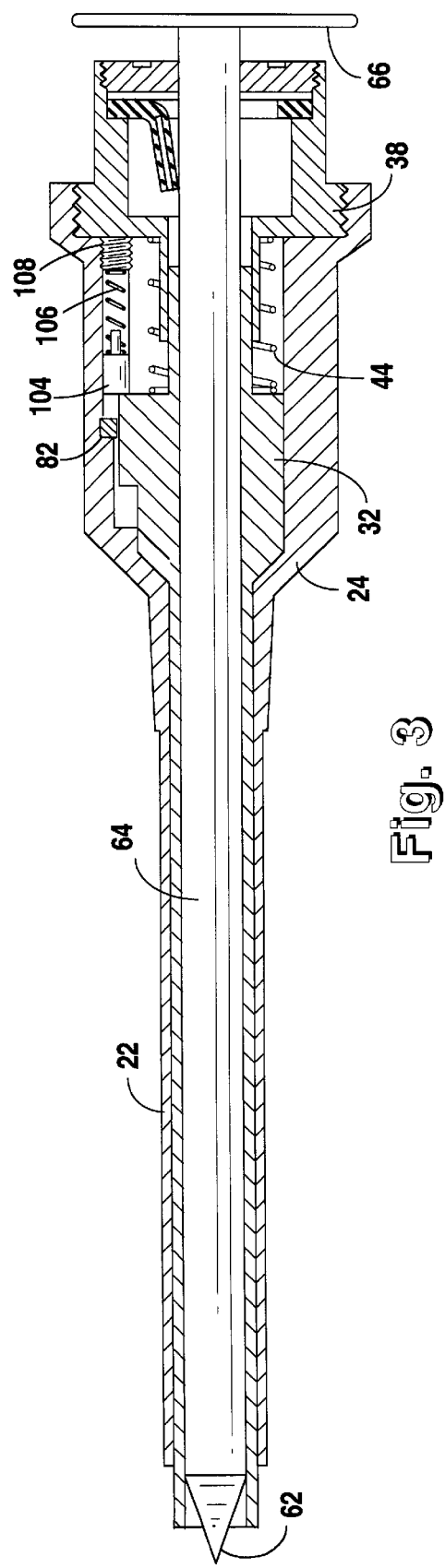

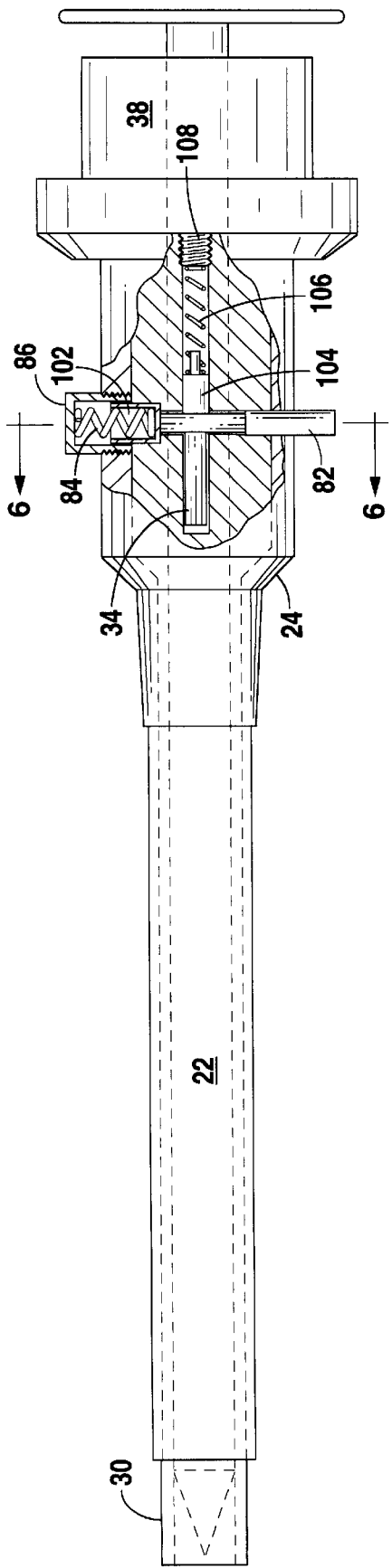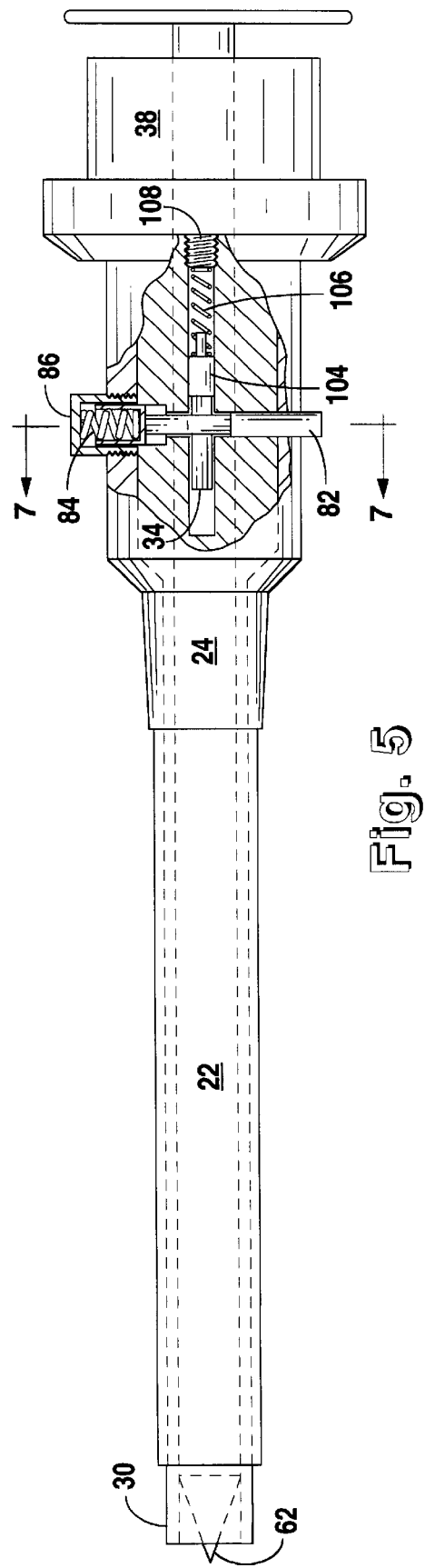

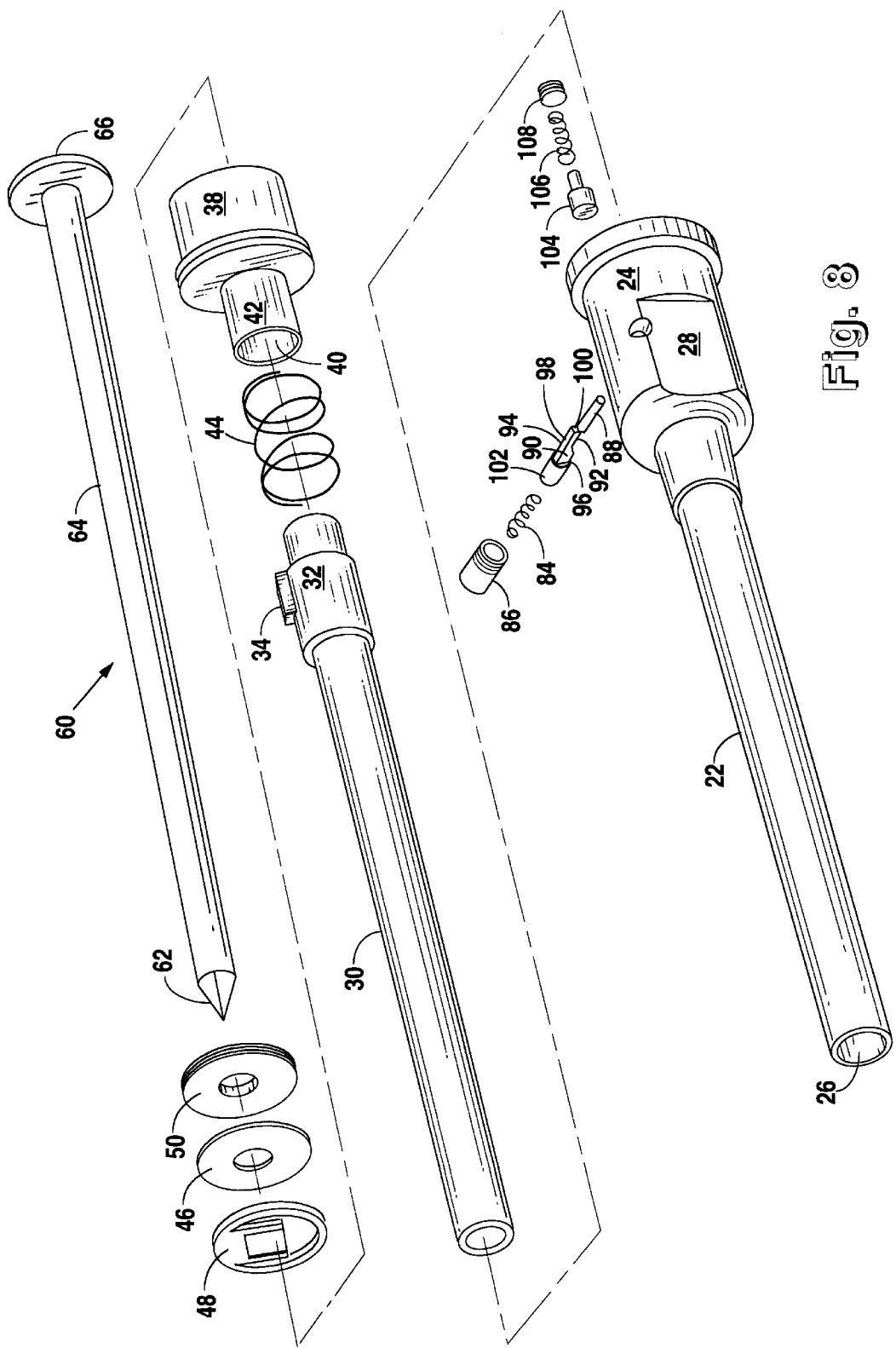

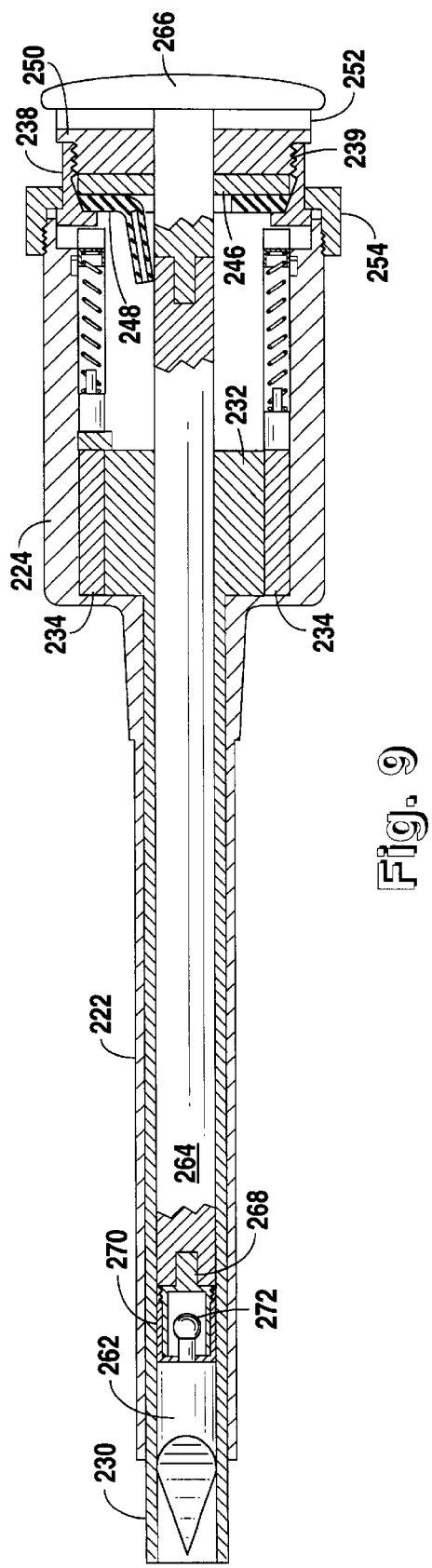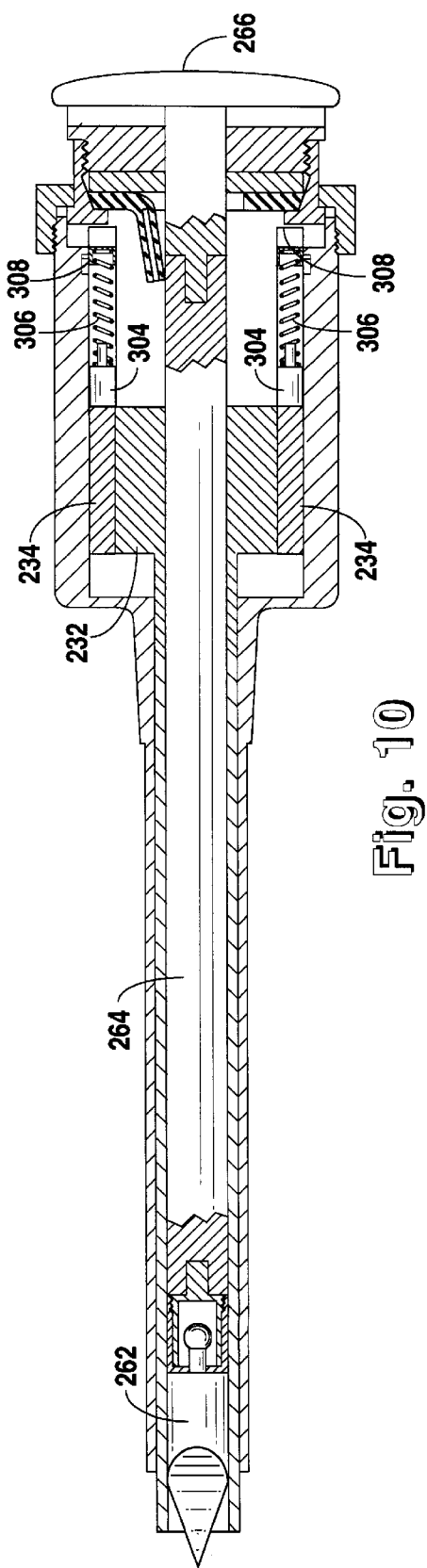

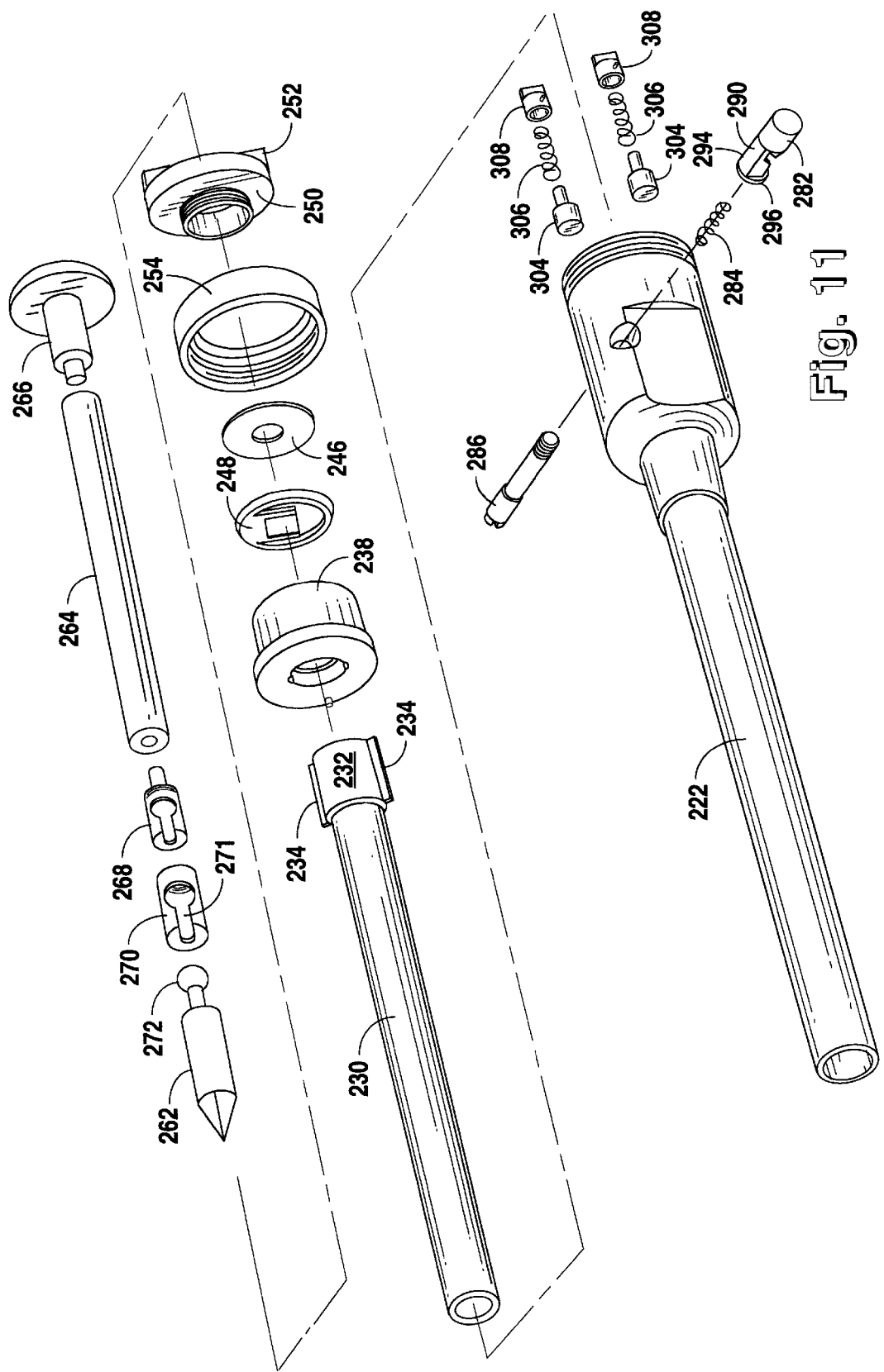

TROCAR INCLUDING AN OBTURATOR WITH A REMOVABLE KNIFE

BACKGROUND OF THE INVENTION

1. Field of the Invention

The present Applicant's invention relates to surgical instruments and, more particularly, to trocars. Trocars are used to pierce or puncture an anatomical cavity to provide communication with the inside of the cavity during a surgical procedure.

2. Background Information

Endoscopic surgery, particularly laparoscopic surgery, is currently becoming a significant method for performing surgeries. It is projected that by the year 2000, half of all surgical procedures will be performed endoscopically. Laparoscopic surgery has become the surgical procedure of choice because of its patient care advantages over "open surgery".

For the past several decades, endoscopic surgery has been available as a method of diagnosis and, for a very limited number of disorders, a treatment. Until recently, a factor limiting the types of surgeries that could be performed laparoscopically was the lack of appropriate instrumentation and the inability to employ intraoperative assistance. In the past, endoscopes allowed only direct visualization by the surgeon, such as the endoscope disclosed in U.S. Pat. No. 4,254,762 issued to Yoon. This led to the situation where the surgeon had one hand holding the laparoscope to his eye and then had only one hand available to operate.

Fortunately, miniaturization of video camera computer chips has led to the development of video cameras that can easily be attached to an endoscope or laparoscope. During surgery, connecting a video camera and monitor to the laparoscope enables all the operating room personnel to view the surgical procedure, rather than just the surgeon. Thus, the operating room personnel are able to provide operative assistance just as they do with open surgery. The type and number of surgical procedures amenable to laparoscopic surgery is presently one of the most rapidly developing areas of surgery.

The pivotal advantage of laparoscopic surgery over open surgery is the decreased post-operative recovery time. In many instances, a patient is able to leave the hospital the same day or within twenty-four hours after laparoscopic surgery has been performed. This is compared to an open surgical procedure that would require several more days of hospitalization. Additionally, laparoscopic surgery provides a decreased incidence of post-operative abdominal adhesions, decreased wound infection rates, and decreased post-operative pain with enhanced cosmetic results.

An essential medical instrument for endoscopic procedures is the trocar. Trocars are sharp, pointed surgical instruments used to puncture the wall of an anatomical cavity. The trocar consists of a tube or cannula and a cutting element called an obturator or stylet. The obturator fits within the cannula and has a sharp piercing tip at its end.

A conventional laparoscopic trocar insertion procedure usually follows insufflation of the abdominal cavity with $CO_2$ gas. The introduction of $CO_2$ gas into the abdominal cavity lifts the abdominal wall away from the internal viscera. Once this is done, the abdominal wall is penetrated with the trocar. After insertion of the trocar through the abdominal wall, the surgeon removes the obturator leaving the cannula or tube protruding through the body wall. A laparoscope or laparoscopic instrument can then be inserted through the cannula to view internal organs or perform surgical procedures.

Penetrating the wall of the abdominal cavity with the trocar is done quickly. The sharp point of the obturator encounters great resistance from the skin, muscle, and tissue membranes of the abdominal wall while it is being pushed through these structures. Once the trocar's sharp point and blade pass through the abdominal wall and into the cavity, the resistance to the trocar drops quickly.

The obturator needs a sharp piercing tip to quickly penetrate the wall of the abdominal cavity. After repeated use, the tip tends to dull, which in some conventional trocars requires the replacement of the entire obturator shaft. Some trocars include a disposable tip mounted upon an obturator shaft, such as the tip disclosed in U.S. Pat. No. 4,601,710 issued to Moll. Disposable tips typically attach to the obturator shaft using screwable threads or set screws. A shortcoming of disposable tipped trocars is that such mounting methods are inadequate and could result in the potentially dangerous situation of the tip becoming dislodged during an operation. The tip either unscrews or detaches from the shaft. Furthermore, detachable set screws may separate from the shaft and become lost within the body. Another shortcoming of disposable tips is that relatively small set screws make mounting of the tip to the shaft difficult.

Accordingly, a trocar having a disposable knife securely and easily attached to the shaft will improve over conventional trocars.

SUMMARY OF THE INVENTION

In accordance with the aims of the present invention, one embodiment of an obturator for a trocar has a shaft, pin, and removable knife. The pin mounts to the shaft and secures the knife thereto.

An object of the present invention is to provide a means by which the trocar knife or cutting edge can easily be replaced after each surgical procedure, thus providing a sharp cutting edge for each surgical use and also minimizing medical waste.

It is another object of the present invention to provide a disposable trocar knife that securely and easily attaches to the shaft.

It is a further object of the present invention to provide a rotatable trocar knife that is secured to the obturator shaft.

It is still a further object of the present invention to provide a fixed trocar knife.

It is still another object of the present invention to provide a safety shield control mechanism that is easy to verify if the safety shield is armed or safe.

An additional object of the present invention is to provide a safety shield that can be tested for proper operation without the obturator being located in the cannula.

It is a further object of the present invention to provide a safety shield that is removable and separable from the obturator.

It is still another object of the present invention to provide a reusable trocar with a safety shield that is easily disassembled, easily cleaned, sterilized, and easily reassembled for reuse.

It is yet another object of the present invention to provide a trocar in which the upper housing can be quickly disassembled from the main housing while in use to allow for unobstructed access through the trocar to the body cavity.

It is an additional object to provide a trocar blade that attaches to the shaft without utilizing detachable parts.

Still other features and advantages to the present invention will be become evident to those skilled in the art in light of the following detailed description of the preferred embodiment.

BRIEF DESCRIPTION OF THE DRAWINGS

FIG. 2 is a cross sectional view of the present invention with the safety shield extended.

FIG. 3 is a cross sectional view of the present invention with the safety shield partially retracted.

FIG. 4 is a cut-away sectional view of the present invention showing the trigger in the safe position.

FIG. 5 is a cut-away sectional view of the present invention showing the trigger in the armed position.

FIG. 8 is an exploded view of the present invention.

FIG. 9 is a cross sectional view of the alternative embodiment shown in FIG. 11 with the safety shield extended.

FIG. 10 is a cross sectional view of the alternative embodiment shown in FIG. 11 with the safety shield partially retracted.

FIG. 11 is an exploded view of an alternative embodiment of the present invention.

DETAILED DESCRIPTION OF THE PREFERRED EMBODIMENT

Figure 1:
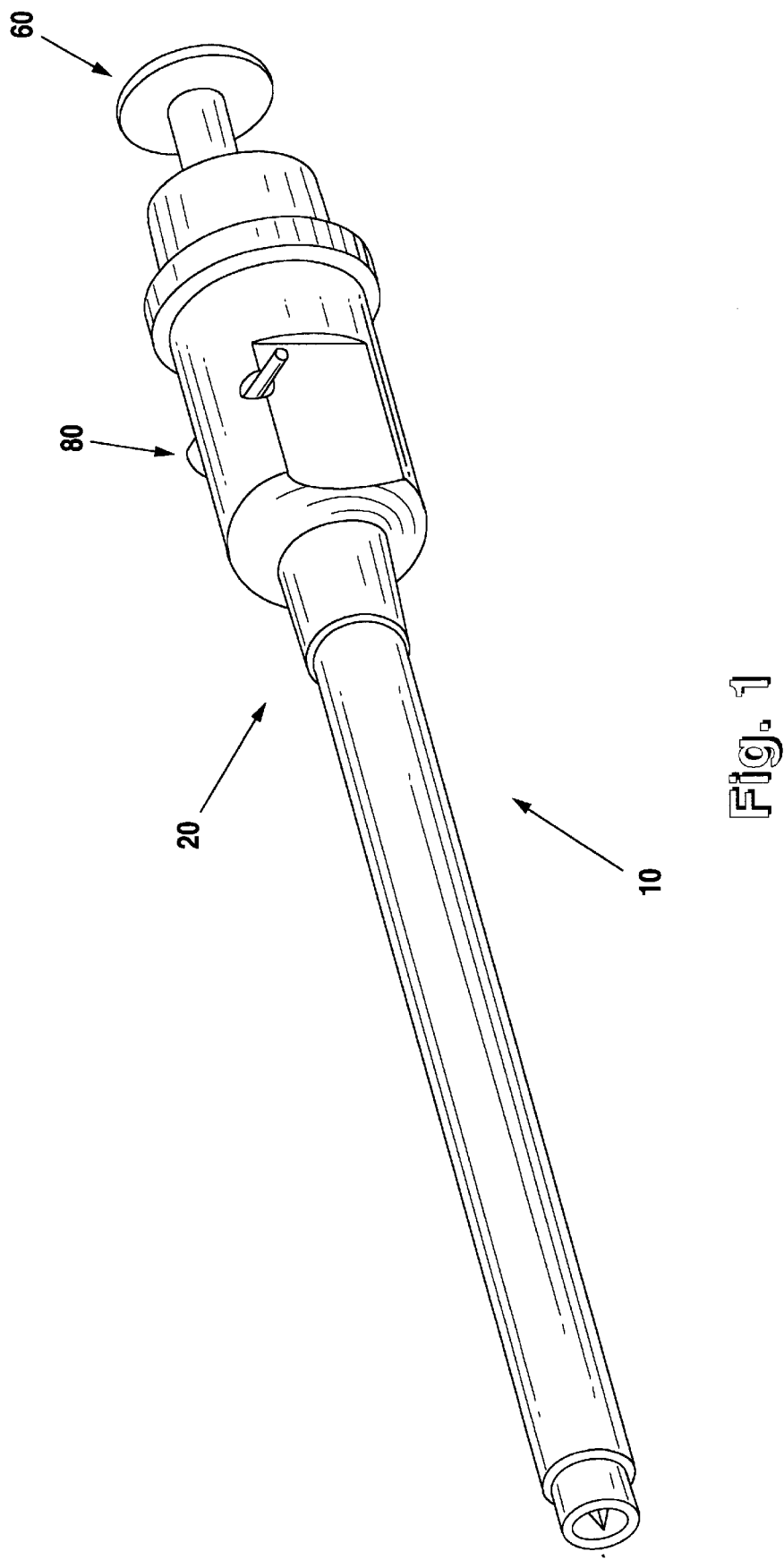
FIG. 1 is a perspective view of the present invention.

Referring now to the drawings, FIGS. 1–8 illustrate a first embodiment of a safety shielded, reusable trocar generally designated (10) consisting of a trocar cannula subassembly (20), a safety shield control mechanism (80), and a separate obturator subassembly (60). The three subassemblies are interfitting, but are designed to be easily disassembled for easy cleaning and sterilizing. To facilitate the reusable features of the trocar (10), it is preferably made from a durable and strong material which can be cleaned and sterilized, such as surgical stainless steel, acetal, polysulfone, or any high temperature thermoplastic. However, any material is acceptable as long as it may be sterilized by gas, autoclave, cold sterilization, and the like.

Referring to FIG. 8, the trocar cannula subassembly (20) includes an outer cannula (22) attached to a main housing (24). The outer cannula (22) may be attached to the main housing (24) in a variety of different methods including the outer cannula (22) being pressed onto the main housing (24), or it may be machined out of the same piece of metal as the main housing (24). The outer cannula (22) and main housing (24) align to have a central axial bore (26) for receiving the inner cannula (30) and the obturator subassembly (60). The central axial bore (26) is larger in the main housing (24) than in the outer cannula (22). Main housing (24) has rectangular recesses (28) to facilitate gripping the trocar with the fingers and for quickly locating the safety shield control mechanism (80).

The inner cannula (30) is a tube adapted to be slidably inserted into the outer cannula (22) and main housing (24), and serves as a safety shield for the obturator subassembly (60). The aft end of the inner cannula (30) has a slider (32) attached which is adapted to allow smooth sliding of the inner cannula (30) in the larger central axial bore of the main housing (24). The slider (32) also serves as a stop to prevent the inner cannula (30) from sliding completely through the main housing (24). The rear end of the slider (32) has an elongated key (34). The inner side of main housing (24) has a keyway (not shown) in which key (34) rides to permit axial movement without rotation of the inner cannula (30) relative to the outer cannula (22) and main housing (24).

As shown in FIGS. 2 and 8, the upper housing (38) is removably secured to the main housing (24). The upper housing (38) has a lower tube (42) with a central axial bore (40) adapted to receive the rear end of inner cannula (30). A spring (44) sits around the rear end of the inner cannula (30) and lower tube (42). Lower tube (42) has its ends seated against the bottom of the upper housing (38) and the top of the slider (32). The spring (42) biases inner cannula (30) in the extended position. The bottom of lower tube (42) serves as a stop to limit the rearward axial movement of inner cannula (30) relative to main housing (24).

Upper housing (38) houses removable sealing means including a removable, upper wiper seal (46) and a removable flapper valve seal (48). The seals are preferably made of durable silicon rubber and plastic which can be sterilized. Wiper seal (46) has a central opening which is approximately equal to the outside diameter of obturator. The primary function of wiper seal (46) is to insure a tight seal when the stem of the shaft of the obturator or other instrument shafts are inserted through upper housing (38). Flapper valve (48) acts as a closure means when the obturator or other instrument is withdrawn and separated from the trocar cannula subassembly (20). Sealing means retainer (50) is removably attached to upper housing (38) and serves as a keeper of the seals to prevent them from falling out of upper housing (38). Sealing means retainer (50) has a central bore longitudinally aligned with the central bore of inner cannula (30) for receiving the shaft of the obturator or other instrument.

The obturator subassembly (60) includes a pyramidal-shaped knife (62), an elongated stem or shaft (64), and an arcuate shaped cap (66). Obturator (60) is adapted to extend and move longitudinally through upper housing (38), main housing (24), outer cannula (22), and inner cannula (30). Inner cannula (30) serves as a safety shield for the knife (62) portion of obturator (60). Obturator (60) may be easily removed from the trocar cannula subassembly (20).

The operator of the inner cannula (30) is controlled by the safety shield control mechanism (80), which is removably located in the main housing (24) and is removably engaged with the inner cannula (30). Safety shield control mechanism (80) provides visual, tactile, and aural signals to the operator allowing for positive and easily verifiable engagement and disengagement of the inner cannula (30) as a safety shield for the obturator knife (62). When the trocar cannula subassembly (20) and safety shield control mechanism (80) are coupled, proper operation of the safety shield can be verified without the obturator subassembly (60) being inserted in the inner cannula (30).

As shown in FIGS. 2 through 7, the safety shield control mechanism (80) includes a trigger pin (82), a trigger spring (84), and red pin (86), which extend perpendicularly through a chamber in the main housing (24). Red pin (86) is removably secured to main housing (24). The ends of trigger spring (84) are seated against the inner face of red pin (86) and the inner face of trigger pin (82) biasing trigger pin (82) in an extended position.

Trigger pin (82) has a finger (88) which extends perpendicularly from main housing (24). Secured to finger (88) is an offset rectangular member (90) having a keyway (92) and an upper face (94) and a lower face (96). Upper face (94) has two steps (98 and 100). Secured to offset rectangular member (90) is a circular housing (102) for receiving trigger spring (84).

Also part of the safety shield control mechanism (80) are a latch pin (104), a latch spring (106), and a latch spring retainer (108) located in the same keyway in main housing (24) as key (34). Latch pin (104) is adapted to abut key (34) to assist in spring biasing inner cannula (30) to the extended position.

Figure 6:
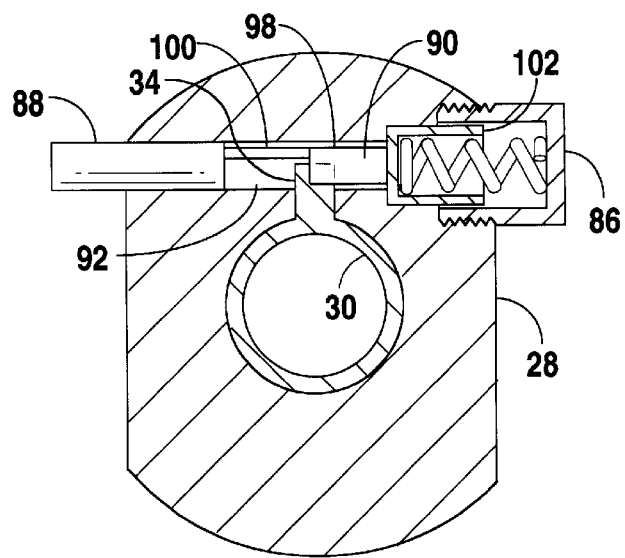
FIG. 6 is a cross sectional view of the present invention taken along line 6—6 of FIG. 4.

In the safe position as shown in FIGS. 2 and 6, trigger pin (82) is trigger spring (84) biased in the extended position so that latch pin (104) is demountably located on the first step (8) of upper face (94) and lower face (96) of offset rectangular member (90). Latch pin (104) prevents key (34) from moving axially rearward, thereby keeping the safety shield extended and locked over obturator knife (62).

Figure 7:
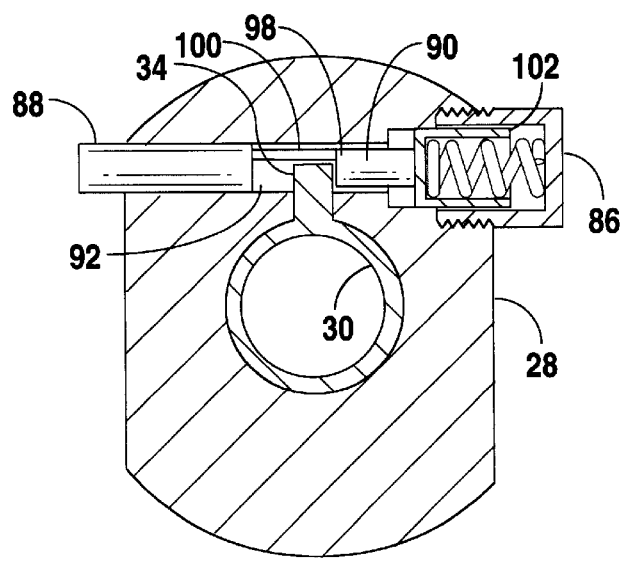
FIG. 7 is a cross sectional view of the present invention taken along line 7—7 of FIG. 5.

To arm, as shown in FIG. 7, trigger pin (82) is pushed in perpendicularly to main housing (24) a sufficient distance to allow latch spring (106) biased latch pin (104) to drop to the second step (100) of upper face (94). Latch pin (104) while on the second step (100) abuts the side of the first step (98) and serves as a latch to prevent perpendicular movement by trigger spring (84), bias trigger pin (82) and keep trigger pin (82) in the armed position. With trigger pin (82) in the armed position, keyway (92) of offset rectangular member (90) is aligned with key (34) of inner cannula (30) thereby allowing inner cannula (30) to move longitudinally inside outer cannula (22). When inner cannula (30) moves rearward, as shown in FIG. 3, key (34) lifts latch pin (104) and trigger pin (82), and biases is trigger spring (84) outwards toward the safe position. As inner cannula (30) moves forward, key (34) moves past trigger pin (82) and first step (98) of offset rectangular member (90), and engages latch pin (104) thereby putting safety shield control mechanism (80) in the safe position.

The safety shielded, reusable trocar (10) operates and is used as follows. Before use, the trocar (10) will typically be in the assembled form as shown in FIGS. 1 and 2 with the inner cannula (30) locked in position as a safety shield for the obturator for safety purposes and storage. In this position, the knife (62), or piercing tip, is shielded and cannot be damaged by inadvertent contact with other surfaces. In this locked position, spring (44) biases inner cannula (30) forward with the forward edges of slider (32) acting as stops against the lower, inner portion of main housing (24) to define the forwardmost position of inner cannula (30). Also in this locked position, lower face (96) of trigger pin (82) acts as a stop against the rearward edges of slider (32) to define the rearmost position of inner cannula (30). Trigger pin (82) is in its extended position as shown in FIGS. 4 and 6. Flapper valve (48) is biased against the shaft (64) of obturator (60) to frictionally minimize longitudinal movement of obturator (60) relative to main housing (24). The inner lip of wiper seal (46) rests snugly against the shaft (64) of obturator (60) and forms a seal therewith.

To unlock inner cannula (30) from its safety shield position, trigger pin (82) is pushed in perpendicularly to main housing (24), as shown in FIGS. 5 and 7. Latch pin (104) moves to the second step (100) of trigger pin (82) and keyway (92) of trigger pin (82) is aligned with key (34) of inner cannula (30). When latch pin (104) moves to the second step (100) of trigger pin (82), an audible click is heard by the operator. In this armed position, inner cannula (30) is free to move longitudinally rearward until stopped by slider (32) abutting the lower tube (42) of upper housing (38).

In surgical use, the trocar (10) is used in conjunction with insufflatory techniques wherein a needle type instrument first punctures the skin in a desired body cavity region. Usually, the needle houses a stylet, or the like, that introduces a gas-like carbon dioxide from a pressurized container into the body cavity. After the cavity has been inflated, a small incision may be made in the skin at the desired body cavity location. The trocar (10) is put in its armed position. The trocar (10) is gripped firmly with the cap (66) of the obturator (60) against the palm of the surgeon's hand. The safety shield portion of the inner cannula (30) is placed against the incision in the skin and firm pressure is exerted against the skin. The pressure causes the inner cannula (30) to be pushed rearwardly against spring (44) to its retracted position as shown in FIG. 3, thereby exposing the knife (62) of the obturator, and key (34) lifts latch pin (104) from the second step (100) of trigger pin (82). The tip of the knife (62) enters the incision and underlying tissue with continued pressure.

Once the knife (62) has penetrated tissue and has entered the cavity, the force against the front end of the inner cannula (30) ceases and the inner cannula (30) is automatically moved longitudinally back to its extended position through the action of spring (44). As inner cannula (30) moves forward, key (34) moves past trigger pin (82) and first step (98) of offset rectangular member (90) engages latch pin (104), thereby putting safety shield control mechanism (80) in the safe and locked position.

The obturator subassembly (60) may be withdrawn from the trocar cannula subassembly (20) once the cavity has been penetrated. During withdrawal, once the tip of the obturator (60) clears the opening in wiper seal (46), flapper valve (48) will bias the flapper to a sealed position. Air pressure within the body cavity is thus maintained. Although not shown, main housing (24) may include a stopcock port into which the nozzle of a stopcock could be inserted to pass additional insufflating gas into the cavity.

The trocar will normally be inserted into the body cavity until main housing (24) abuts the skin. After the obturator subassembly (60) has been separated from the trocar cannula subassembly (20), surgical instruments may be inserted into the body cavity via the central bore (26) of trocar cannula subassembly (20) to view internal tissues, perform operations thereon, or drain bodily fluids.

If the surgeon desires obstructed access to the body cavity for better viewing or to take a tissue sample, upper housing (38) may be removed from main housing (24). By removing upper housing (38), the wiper seal (46), flapper seal, and seal retainer (50) are all removed as a single unit. The trocar cannula subassembly (20) then provides unobstructed access to the body cavity to permit removal of specimens and to deflate the cavity.

After use, the entire trocar (10) can be easily disassembled for cleaning, sterilization, and ready for reuse. Sterilization can be by any standard sterilization technique.

An alternative embodiment of the present invention is illustrated in FIGS. 9–12. Although the function and operation of the safety shielded, reusable trocar are the same, there are slight changes to each subassembly unit.

The trocar cannula subassembly (220) includes an inner cannula (230) having a slider (232) located flush with the rearmost end of the inner cannula (230). A pair of diametrically opposed axially elongated keys (234) are attached to slider (232). The interior of main housing (224) has complementary keyways (not shown) for receiving keys (234) and allowing longitudinal movement of inner cannula (230) without any rotational movement of inner cannula (230) relative to main housing (224) and outer cannula (222). A pair of diametrically opposed latch spring mechanisms, located in keyways, are removable. Latch spring mechanisms include a latch pin (304), latch spring (306), and a latch spring retainer (308). Latch spring mechanisms are adapted to abut keys (234) to spring bias inner cannula (230) to the extended position. The interaction between the latch spring mechanism, trigger pin (282), and keys (234) is as described above for the first embodiment of the present invention.

Upper housing (238) has a bevelled interior surface (239) to house sealing means such as a flapper valve (248) and wiper valve (246). The edges of flapper valve (248) are complementarily bevelled so that the sealing means can only be inserted with flapper valve (248) closest to inner cannula (230). If the sealing means would be reversed, the sealing means would not fit into upper housing (238). Sealing means are kept in place by a sealing means retainer (250) having a handle (252) to provide easy removable securing to upper housing (238). Upper housing (238) is removably engaged between a lock ring (254), which couples to main housing (224), as shown in FIGS. 9 and 10.

A second obturator subassembly (260) has a cap (266) secured to a shaft (264). Though the obturator subassembly (260) is shown in use with the trocar cannula subassembly (220) in FIG. 11, it may also be used with trocar cannula subassembly (20). To reduce the overall weight of the trocar, the shaft (264) may be made of a lightweight and durable material such as aluminum. Secured to the opposite end of shaft (264) is a capture fitting (268) for receiving the rounded end (272) of the knife (262). The knife (262) may be made of stainless steel, or alternatively, to further reduce the overall weight, the knife (262) may be made of high temperature thermoplastic. This also gives the additional advantage of making the knife (262) easily replaceable and interchangeable to ensure that the knife is always sharp.

The knife (262) is rotatably and removably secured to the shaft (264) by means of a capture fitting (268) and capture nut (270) arrangement. As best seen in FIG. 11, capture fitting (268) and capture nut (270) are aligned to form an opening (271) for receiving the rounded end of the knife (262). The knife (262) is inserted sideways through opening (271). The capture nut (270) is then rotated at least thirty degrees to rotatably lock knife (262) to the shaft (264), as shown in FIG. 9. This rotatable connection facilitates a smooth incision through the skin as the rotatable knife (262) rotates to counter any rotation of the trocar by the surgeon while applying pressure to the skin.

As shown by FIGS. 13–16, a third or preferred obturator subassembly (460) includes a first knife (480), a shaft (500), a connecting member or pivot pin (510), a cap (520), and a pin (540). The obturator subassembly (460) can be used with either the trocar cannula subassembly (20) or trocar subassembly (220). To reduce the overall weight of the trocar, the shaft (500) may be made of a light weight and durable material such as aluminum. The knife (480) may be made of stainless steel, or alternatively, to further reduce overall weight, the knife (480) may be made of high temperature thermal plastic. This also gives the additional advantage of making the knife (480) easily replaceable and interchangeable to insure that the knife is always sharp.

The shaft (500) includes a slot (502), a substantially cylindrical chamber (504), holes (505a–b), an arcuate recess (506), and an end protrusion (508). The slot (502), substantially cylindrical chamber (504), and arcuate recess (506) together form a cavity for positioning a portion of the knife (480) and substantially all of the pin (540) therein. The pin (540) has an elongated member (542), bulge (544), aperture (546), and a protruding tip (548). Preferably, the elongated member (542) is substantially straight. The pivot pin (510) extends through holes (505a–b) and the aperture (546) within the bulge (544) for fastening the pin (540) to the shaft (500).

The knife (480) includes a head (482) terminating in a point and a neck (488) having a substantially circular groove (486). The neck (484) inserts into the substantially cylindrical chamber (504) of the shaft (506) for mounting the knife (480) thereto.

A cap (520) mounts upon the end protrusion (508) of the shaft (500). The cap (520) includes a capture ring (522) integrally formed with a rounded end (524). The capture ring (522) mounts upon the end protrusion (508) for fastening the cap (520) to the shaft (500).

The pin (540) pivots between a first or interlocked position (540a) and a second or disengaged position (540b). The knife (480) is inserted into the shaft (500) by applying pressure to the end (549) of the pin (540) opposite of the protruding tip (548). As the end (549) moves downward into the recess (506), the protruding tip (548) pivots upward. The first knife (480) mounts to the shaft (500) by inserting the neck (484) of the knife (480) into the chamber (504). Releasing pressure from the end (549) lowers the protruding tip (548) of the pin (540) into the groove (486) of the first knife (480). This interlocked connection with the pin (540) permits rotatable movement of the knife (480) about a longitudinal axis (509) of the shaft (500). Some doctors prefer a rotatable knife to prevent tearing of the skin when inserting an obturator therethrough. Applying pressure to the end (549) disengages the protruding tip (548) from the neck (484) for removing the knife (480).

Alternatively, a second knife (580) may be used with the third obturator assembly (460). The second knife (580) may be made of the same materials as the first knife (480). The second knife (580) includes a head (582) terminating in a point and a substantially circular neck (584) having an aperture (586) therethrough. The second knife (580) mounts to shaft (500) in the same manner as the first knife (480). However, the protruding tip (548) inserts into the aperture (586) for securing the non-rotatable second knife (580). This insertable connection prevents rotation of the knife (580), which some doctors prefer when inserting an obturator through the skin.

Figure 12:
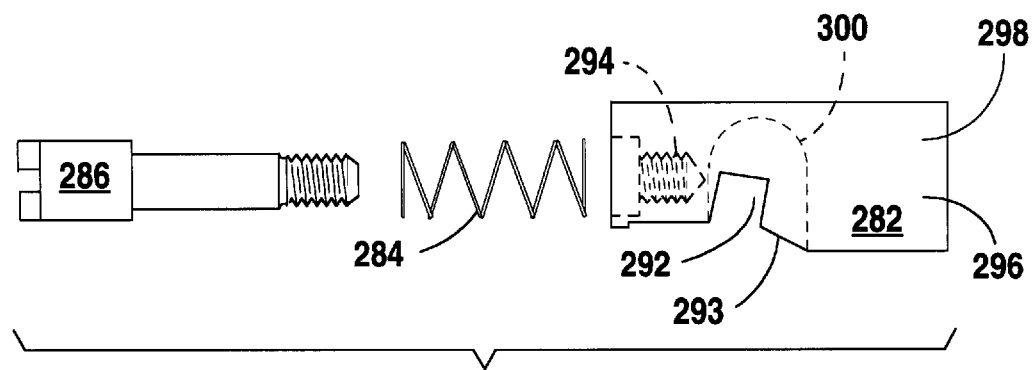
FIG. 12 is an exploded view of the trigger mechanism of the alternative embodiment shown in FIG. 11.
Figure 13:
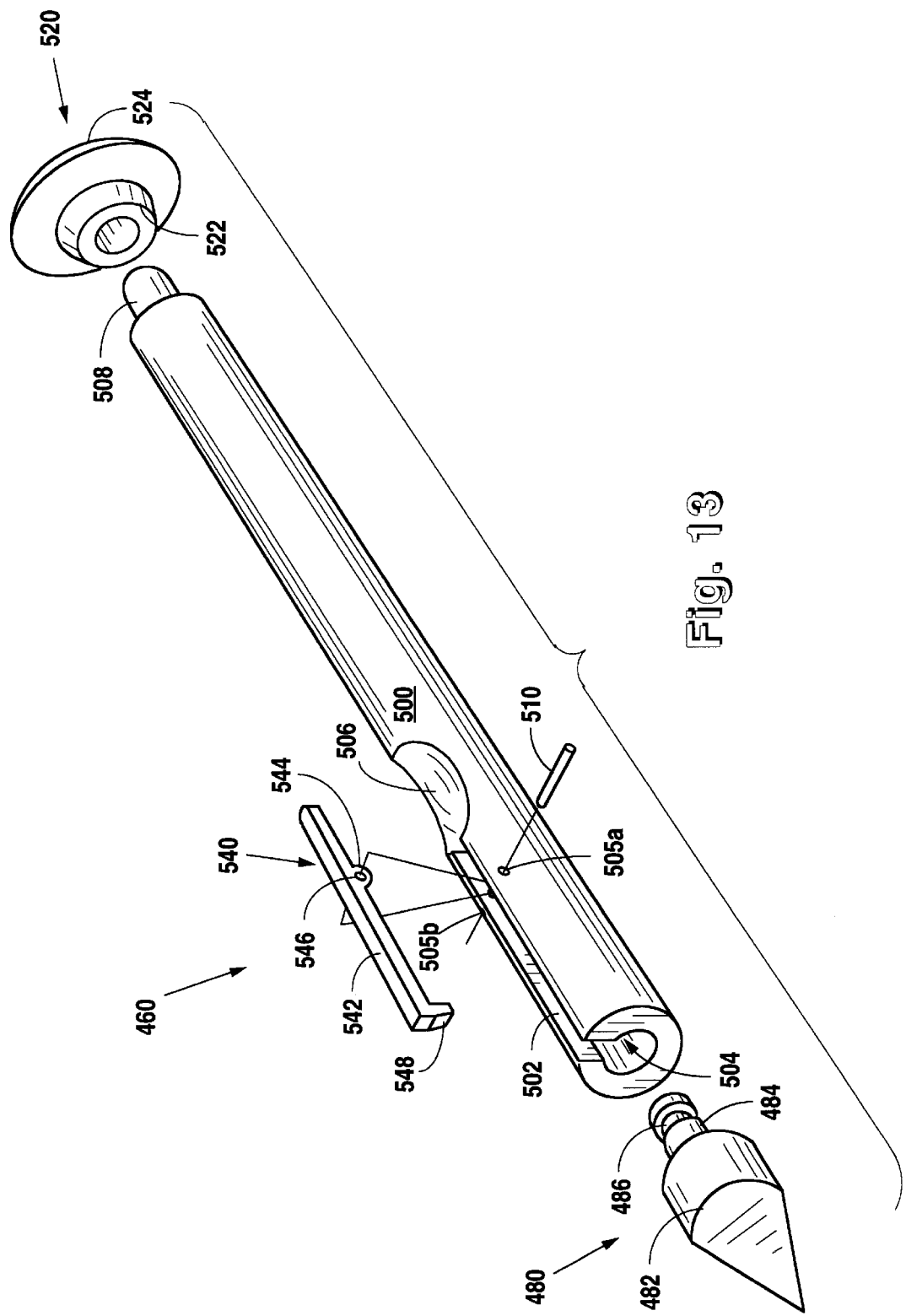
FIG. 13 is an exploded view of a third obturator subassembly.
Figure 14:
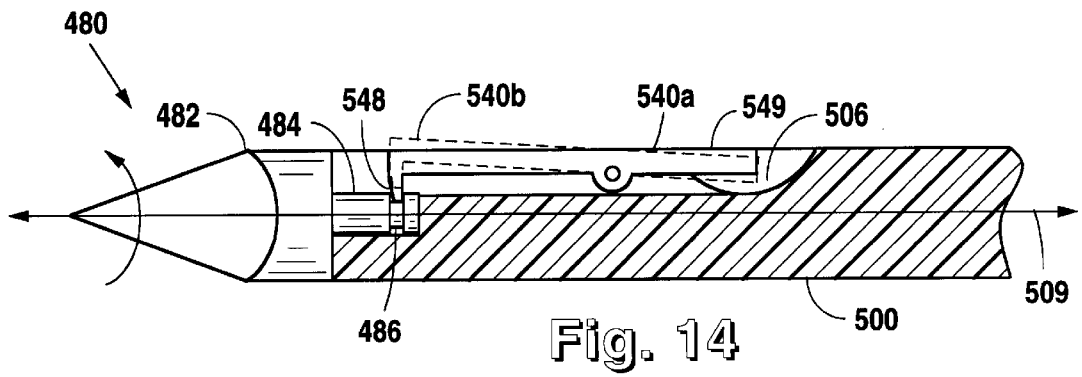
FIG. 14 is a cut-away, cross-sectional view illustrating the pin in first and second positions.
Figure 15:
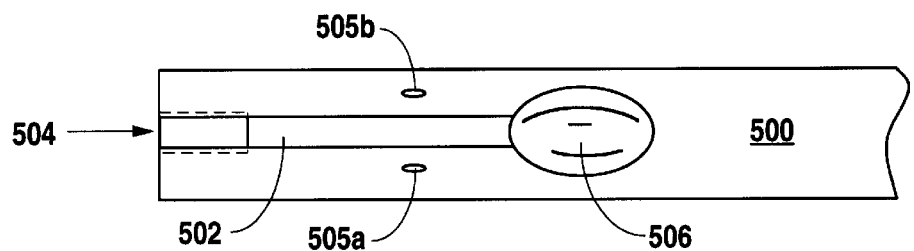
FIG. 15 is a top plan, cut-away view of the shaft.
Figure 16:
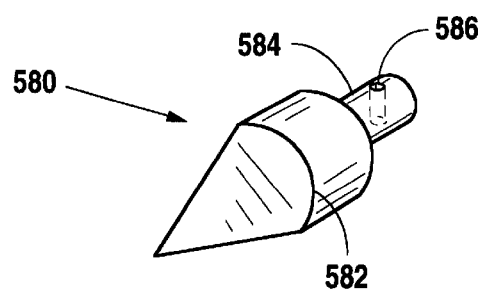
FIG. 16 is an alternative embodiment of a second knife to be used with the third obturator subassembly.

The safety shield control mechanism (280) operates in the same manner as described above. However, the trigger pin has been modified as shown in FIGS. 11 and 12. The trigger pin (282) is now designed to move in and out of both sides of the main housing (224), much like a safety on a rifle. In the armed position, the pin (286) protrudes from the main housing (224) and may be painted the color red. In the safe position, the trigger pin (282) protrudes from the main housing (224) and may be colored green or black. Additionally, the offset rectangular member (290) has been modified for the upper face (294) to have an arcuate shaped second step (300) and the lower face has an angled keyway (292) with a bevelled side surface (293). The bevelled side surface (293) allows for smoother lifting and dropping of the latch pin (304).

In operation of the alternative embodiment, the steps are the same as previously described.

We claim:

1. An obturator for a trocar, comprising:
   a shaft;
   a pin mounted to said shaft;
   a removable knife secured to said shaft by said pin, wherein said pin is pivotable relative to said shaft between a first position that engages said knife and a second position that disengages said pin from said knife.

2. The obturator of claim 1, wherein said knife is rotatable with respect to said shaft.

3. The obturator of claim 1, wherein said knife is fixed with respect to said shaft.

4. The obturator of claim 1, wherein said knife further comprises:
   a head; and
   a neck integrally formed with said head and said neck having a substantially circular groove.

5. The obturator of claim 1, wherein said knife further comprises:
   a head; and
   a neck integrally formed with said head and said neck having an aperture therethrough.

6. A trocar, comprising:
   a cannula;
   an obturator substantially housed within said cannula, said obturator further comprises:
      a shaft;
      a removable knife mountable to said shaft; and
         a pin mounted to said shaft wherein said pin is pivotable relative to said shaft between a first position to engage said knife and a second position to disengage said knife and said pin further comprises:
      an elongated member;
      a tip extending from said member; and
         a bulge extending from said member and having an aperture therethrough.

7. An obturator comprising:
   a shaft;
   a removable knife mountable to said shaft; and
   a pin mounted to said shaft wherein said pin is pivotable relative to said shaft between a first position to engage said knife and a second position to disengage said knife and said pin further comprises:
      an elongated member;
      a tip extending from said member; and
      a bulge extending from said member and having an aperture therethrough.

* * * * *